(12) United States Patent
Anderson et al.

(10) Patent No.: US 9,393,073 B2
(45) Date of Patent: Jul. 19, 2016

(54) METHOD AND APPARATUS FOR SELECTIVE PHOTOTHERMOLYSIS OF VEINS

(71) Applicant: The General Hospital Corporation, Boston, MA (US)

(72) Inventors: Richard R. Anderson, Boston, MA (US); Iris Kedar Rubin, Potomac, MD (US); William A. Farinelli, Danvers, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/828,327

(22) Filed: Aug. 17, 2015

(65) Prior Publication Data

US 2015/0351840 A1     Dec. 10, 2015

Related U.S. Application Data

(60) Division of application No. 13/948,971, filed on Jul. 23, 2013, now Pat. No. 9,138,294, which is a continuation of application No. 13/423,985, filed on Mar. 19, 2012, now abandoned, which is a division of application No. 11/623,383, filed on Jan. 16, 2007, now abandoned.

(51) Int. Cl.
*A61B 18/20* (2006.01)
*A61B 18/00* (2006.01)
*A61N 5/06* (2006.01)

(52) U.S. Cl.
CPC .............. *A61B 18/20* (2013.01); *A61B 18/203* (2013.01); *A61B 2018/00452* (2013.01); *A61B 2018/00458* (2013.01); *A61N 2005/0659* (2013.01)

(58) Field of Classification Search
CPC .................... A61B 18/203; A61B 18/1402
USPC ........................ 606/2–9; 607/88, 89
See application file for complete search history.

(56) References Cited

U.S. PATENT DOCUMENTS 5,147,349 A   9/1992   Johnson et al.
5,759,200 A   6/1998   Azar
(Continued)

FOREIGN PATENT DOCUMENTS

DE    19521003    8/1996
WO    2004053533  6/2004
WO    2005053773  6/2005

OTHER PUBLICATIONS

Ho, Sun Wai et al.: "Treatment of Port Wine Stains with Intense Pulsed Light: A Prospective Study." Dermatological Surgery, 2004, vol. 30, Issue 6, pp. 887.

(Continued)

*Primary Examiner* — William Thomson
*Assistant Examiner* — Jeffrey Lipitz
(74) *Attorney, Agent, or Firm* — Yadov Sidorin; Quarles & Brady, LLP

(57) ABSTRACT

A system and method are provided that are capable of selectively treating a vein using photothermolysis techniques, where an electromagnetic radiation is applied to tissue containing the vein. The radiation can be selected so that it may be more effectively absorbed by veins as compared to arteries. Thus, unwanted thermal damage to arteries in the vicinity of the vein being treated can be reduced or avoided. The radiation can have a frequency of approximately 654 nm, which can provide a ratio of absorption by veins to absorption by arteries of about 3.7. Other wavelengths near 654 nm may be provided, for example, which can have an absorption ratio greater than, e.g., about 3.3 to 3.6.

12 Claims, 3 Drawing Sheets

(56) References Cited

U.S. PATENT DOCUMENTS

| | | |
|---|---|---|
| 5,820,626 A | 10/1998 | Baumgardner |
| 5,824,023 A | 10/1998 | Anderson |
| 5,843,072 A | 12/1998 | Furumoto et al. |
| 6,122,536 A | 9/2000 | Sun et al. |
| 6,214,034 B1 | 4/2001 | Azar |
| 6,358,242 B1 | 3/2002 | Cecchetti |
| 6,398,777 B1 | 6/2002 | Navarro et al. |
| 6,413,267 B1 | 7/2002 | Dumoulin-White et al. |
| 6,595,985 B1 | 7/2003 | Tobinick |
| 6,613,042 B1 | 9/2003 | Tankovich et al. |
| 6,676,655 B2 | 1/2004 | McDaniel |
| 6,746,444 B2 | 6/2004 | Key |
| 6,796,994 B2 | 9/2004 | Ignatius et al. |
| 6,887,260 B1 | 5/2005 | McDaniel |
| 2002/0019625 A1 | 2/2002 | Azar |
| 2003/0097122 A1 | 5/2003 | Ganz et al. |
| 2003/0216795 A1 | 11/2003 | Harth et al. |
| 2004/0073277 A1 | 4/2004 | Geronemus et al. |
| 2004/0116909 A1 | 6/2004 | Neuberger et al. |
| 2004/0167499 A1 | 8/2004 | Grove et al. |
| 2005/0177141 A1 | 8/2005 | Davenport et al. |
| 2005/0203593 A1 | 9/2005 | Shanks et al. |
| 2005/0240168 A1 | 10/2005 | Neuberger et al. |
| 2005/0259942 A1 | 11/2005 | Temelkuran et al. |
| 2006/0134048 A1 | 6/2006 | Shander et al. |
| 2006/0206173 A1 | 9/2006 | Gertner et al. |
| 2007/0191821 A1 | 8/2007 | Boxer Wachler |
| 2008/0172111 A1 | 7/2008 | Anderson |
| 2008/0215039 A1 | 9/2008 | Slatkine et al. |
| 2010/0298911 A1 | 11/2010 | Shafirstein |

OTHER PUBLICATIONS

Yung, A. et al.: "A Comparative Study of a 595-nm with a 585-nm Pulsed Dye Laser in Refractory Port Wine Stains." British Journal of Dermatology, 2005, 153, pp. 601-606.

Hsia, J. et al.: "Treatment of Leg Telangiectasia Using a Long-Pulse Dye Laser at 595 nm." Journal of Lasers in Surgery and Medicine, 1997, 20, pp. 1-5.

Tang, S.V., et al.: "In Vivo Spectrophotometric Evaluation of Normal, Lesional, and Laser-Treated Skin in Patients with Port-Wine Stains." The Journal of Investigative Dermatology, 1983, vol. 80, No. 5, pp. 420-423.

Edstrom, D.W., et al.: "The Treatment of Port-Wine Stains with the Pulsed Dye Laser at 600nm." British Journal of Dermatology, 1997, 136, pp. 360-363.

United States Patent and Trademark Office, Office Action Summary and Detailed Action, U.S. Appl. No. 13/423,985, Jan. 28, 2013.

International Search Report and Written Opinion for PCT/US09/39153 Mailed Sep. 23, 2009.

Kimel et al., "Vascular Response to Laser Photothermolysis as a Function of Pulse Duration, Vessel Type, and Diameter: Implications for Port Wine Stain Laser Therapy"< Lasers Surg. Med., 30, 2002, pp. 161-169.

Wali, "Oxygenation of blood in varicose veins," Afr. J. Med. med. Sci. (2002), 31, 219-222.

Scott et al., "Reappraisal of the oxygenation of blood in varicose veins," Br. J. Surg. 1990, vol. 77, August, 934-936.

METHOD AND APPARATUS FOR SELECTIVE PHOTOTHERMOLYSIS OF VEINS

CROSS-REFERENCE TO RELATED APPLICATIONS

The present application is a divisional of the U.S. patent application Ser. No. 13/948,971 filed on Jul. 23, 2013, now published as U.S. 2013/0310818, which is a continuation of the U.S. patent application Ser. No. 13/423,985 filed on Mar. 19, 2012 and now abandoned, which is a divisional of the U.S. patent application Ser. No. 11/623,383, filed on Jan. 16, 2007 and now abandoned. The disclosure of each of the above-mentioned applications is incorporated herein by reference in its entirety.

FIELD OF INVENTION

The present invention relates to methods and apparatus for a selective photocoagulation of veins, for example, a treatment of port wine stains or varicose veins, while avoiding significant thermal damage to arteries.

BACKGROUND

A blood vessel can be any vascular structure, e.g., an artery, a vein, or a capillary. A dilated or malformed vein can be associated with one or more of a variety of disease conditions such as, e.g., port wine stains and varicose veins.

Port wine stains can include post-capillary venules. Port wine stains can begin in infancy, and may both thicken and darken in color with time. In addition to being disfiguring, port wine stains can have adverse psychosocial effects. A conventional treatment for port wine stains may use a pulsed dye laser at a wavelength of 595 nm. A success rate for complete clearance of port wine stains may be low when using conventional treatment modalities such as the 595 nm pulsed dye laser, which can result from inadequate depth of penetration. Deep vessels can be targeted using, e.g., a 1064 nm Nd:YAG laser treatment for port wine stains. However, a wavelength of 1064 nm can be more strongly absorbed by arterial blood (which may contain primarily oxygenated hemoglobin ("HbO2")), than by venous blood (which may contain a mix of deoxygenated hemoglobin ("Hb") and HbO2)). Thus use of the Nd:YAG laser to treat port wine stains may create undesirable arterial damage, causing tissue necrosis and scarring, and can be dangerous to a patient. Although radiation from a 595 nm pulsed dye laser may be somewhat more absorbed by deoxygenated hemoglobin (Hb) than by oxygenated hemoglobin (HbO2), treatment fluence with the pulsed dye laser can still be limited by potential thermal damage to arteries. It may be desirable to have a laser that is designed specifically to target deoxygenated hemoglobin (Hb), and can be significantly more selective for veins.

Varicose veins can be dilated, tortuous veins which may result from defective structure or function of the valves of the veins, from intrinsic weakness of a vein wall, or from arteriovenous fistulas. Varicose veins can be categorized as superficial or deep. Superficial varicose veins may be primary, originating in the superficial system, or secondary, resulting from deep venous insufficiency and incompetent perforating veins, or from deep venous occlusions causing enlargement of superficial veins that can serve as collateral veins.

Superficial varicose veins may provide an undesirable cosmetic appearance. Conventional treatments for superficial varicose veins can include sclerotherapy or surgical therapy. For example, sclerotherapy can include injection of a sclerosing solution such as hypertonic saline or surfactants into blood vessels of interest, which may result in deformation of the vascular structure. Surgical therapy can involve extensive ligation and stripping of greater and lesser saphenous veins. However, an administration of such therapies can use a high degree of technical skill. Also, a fear of needles and/or surgical procedures may prevent many patients from seeking these treatments.

Lasers and other light sources can be used in photothermolysis therapy to treat dilated blood vessels, such as superficial varicose veins. Photothermolysis treatment techniques are described, e.g., in U.S. Pat. No. 5,558,667. Absorbed light, which can be provided in a form of pulses, may be used to damage the vessels while sparing surrounding tissues. For example, an irradiation of a blood vessel with an electromagnetic radiation can lead to an absorption of energy by blood components contained therein and subsequent heating of the vessel. The heated vessel may thrombose and collapse, which can produce desired therapeutic effects for treatment of venous malformations. However, nearby arteries may also be damaged by such photothermolysis techniques, which can lead to partial or complete closure of the arteries, necrosis of adjacent tissue, and unwanted scarring.

A reperfusion of treated blood vessels may reduce the effectiveness of photothermolysis treatment. Multiple treatments can be preferred because of the reperfusion of a treated vessel, which can become more likely if the amount of applied energy is limited to avoid unwanted damage to nearby arteries. High costs, number of treatments, and risk of post-treatment pigmentation are other negative factors which may be associated with photothermolysis therapy.

Superficial varicose veins may be treated using sclerotherapy, which can be effective but is often painful, and can have side effects including, e.g., hyperpigmentation, matting, and/or ulceration. Various lasers may be used for treating ectatic leg veins such as, e.g., a pulsed dye laser operating at a wavelength of 595 nm, an alexandrite laser at 755 nm, a diode laser at 800/810 nm, or a NdYag laser at 1064 nm, although the use of such lasers may not be very effective and/or may produce undesirable side effects. A phototreatment of veins using lasers or other sources of electromagnetic radiation such as, e.g., Intense Pulsed Light ("IPL") sources, may also induce unwanted thermal damage to nearby arteries.

Therefore, it may be desirable to provide a laser or IPL source that can selectively photocoagulate veins for treatment of various venous malformations, with relative sparing of arteries.

SUMMARY OF THE INVENTION

Exemplary method and apparatus of the present invention can provide, e.g., selective photothermolysis of venous lesions using a laser, IPL source or other source of electromagnetic radiation which can facilitate a relative sparing of arteries.

According to exemplary embodiments of the present invention, a method can be provided for treating a vein, which includes directing an electromagnetic radiation to biological tissue, such as skin, containing the vein. Characteristics of the radiation can be chosen so the radiation may be selectively absorbed by veins as compared with arteries. For example, the radiation has a wavelength between about 632 nm and 680 nm, between about 638 nm and 668 nm, between about 644 nm and 662 nm, or about 654 nm.

In certain exemplary embodiments of the present invention, the radiation can be provided by a pulsed dye laser, another type of laser, or an intense pulsed light source.

Veins and vascular lesions which can be treated using exemplary embodiments of the present invention can include but are not limited to varicose veins and port wine stains. Venous malformations in organs other than the skin may also be treated using exemplary embodiments of the present invention.

According to further exemplary embodiments of the present invention, a system can be provided which is configured to treat a vein using photothermolysis techniques. For example, characteristics of the radiation can be chosen so the radiation is selectively absorbed by veins as compared with arteries to avoid unwanted arterial damage. The exemplary system can include, e.g., a radiation source, a power source, control electronics, and an optional optical arrangement which can be used to further direct the radiation toward the tissue being treated. The exemplary system can also include an arrangement configured to cool the surface of the tissue being treated.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which.

While the present invention will now be described in detail with reference to the figures, it is done so in connection with the illustrative embodiments.

DETAILED DESCRIPTION

Perfusion (blood flow) can maintain a blood vessel such as, e.g., a vein or an artery, in a healthy condition. Perfusion of blood can be an important function of blood vessels. Conversely, when a vessel is closed off and perfusion stops, the vessel may eventually thrombose, die, and degrade. It may be desirable to reduce or eliminate perfusion in certain blood vessels, e.g., in venous malformations, for therapeutic and/or cosmetic purposes. Non-invasive methods using photothermolysis can be provided to make selective use of this natural process.

For example, a vascular structure may be irradiated with electromagnetic radiation using a photothermolysis procedure. Blood vessels contain red blood cells which are rich in hemoglobin. Hemoglobin can provide a chromophore that may be absent in the surrounding tissues, e.g., the dermis, and which may preferentially absorb radiation. Therefore, hemoglobin can be a suitable target for selective absorption of heat energy within blood vessels. For example, deoxygenated hemoglobin (deoxyhemoglobin, or Hb) and/or oxygenated hemoglobin (oxyhemoglobin, or HbO2) can preferentially absorb radiation, which can lead to local heating of the structure. Such a heating may thermally damage the blood vessel, and lead to a reduction or elimination of perfusion therein.

It may be preferable to use photothermolysis techniques to damage veins such as, e.g., varicose veins, or post-capillary venules which may be present in port wine stains. However, conventional photothermolysis techniques may also produce unwanted thermal damage to nearby arteries, which can lead to undesirable effects such as, e.g., local necrosis and scarring.

According to exemplary embodiments of the present invention, a system and method can be provided for photothermolysis of venous structures which can avoid inducing a significant thermal damage in arteries. Arterial blood can contain predominantly oxygenated hemoglobin, whereas venous blood can include a mix of oxygenated and deoxygenated hemoglobin. Photothermolysis using an electromagnetic radiation that is more strongly absorbed by Hb than by HbO2 can be used to induce significant thermal damage in particular veins while avoiding or inducing lesser thermal damage in nearby arteries.

Figure 1:
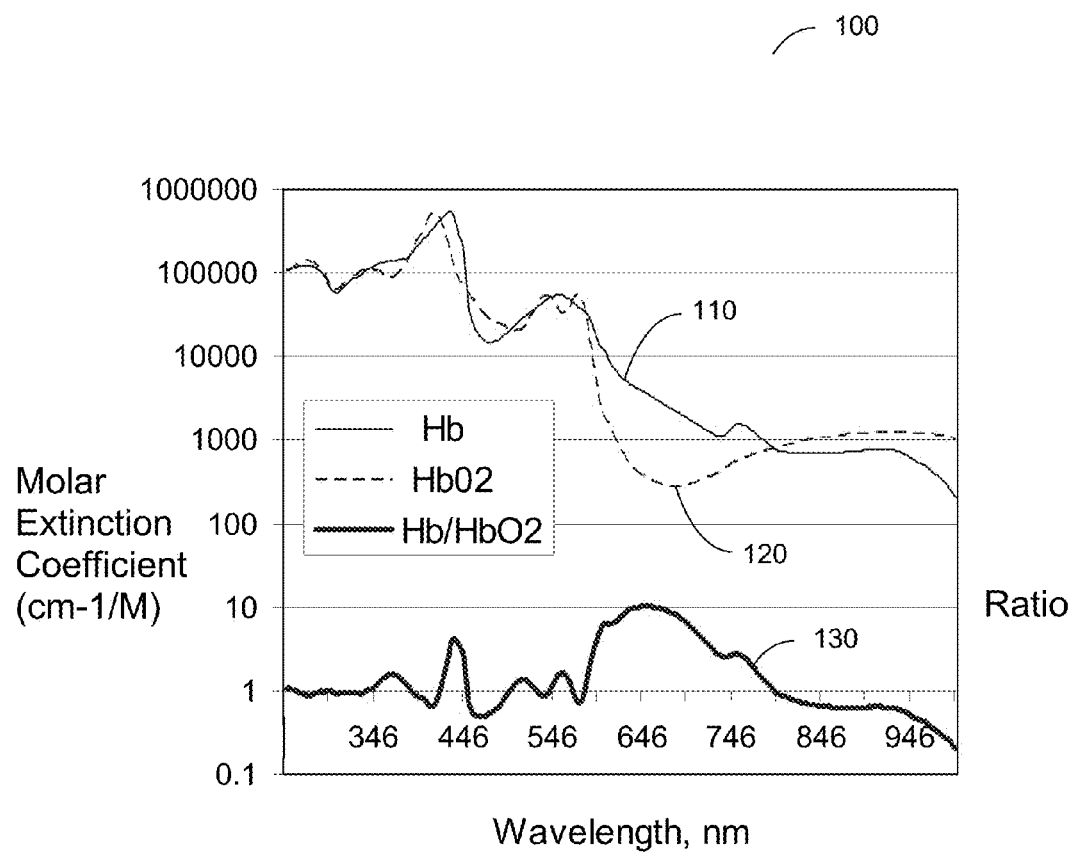
FIG. 1 is an exemplary graph of an absorption of electromagnetic energy by Hb and HbO2 as a function of wavelength of the energy, together with an absorption ratio of Hb and HbO2.

FIG. 1 is an exemplary graph 100 of absorption of deoxyhemoglobin 110 and of oxyhemoglobin 120 as a function of electromagnetic energy wavelength. Also shown in FIG. 1 is a graph of a ratio 130 of the absorption of the electromagnetic energy by deoxyhemoglobin 110 to the absorption by oxyhemoglobin 120. This graph indicates that the Hb/HbO2 absorption ratio is larger for electromagnetic radiation having wavelengths between about 600 nm and 700 nm.

Table 1 provides numerical values of absorption by Hb ("UHb") and by HbO2 (UhbO2") of electromagnetic radiation having wavelengths between 620 nm and 680 nm. Table 1 shows a maximum UHb/UHbO2 absorption ratio of about 10.23 at a wavelength of 654 nm. This absorption ratio can be greater than 10 for wavelengths between about 644 nm and 662 nm. Further, the UHb/UHbO2 absorption ratio may be greater than about 9 for wavelengths between about 634 nm and 676 nm.

Veins can typically contain approximately 30% deoxyhemoglobin (Hb) and 70% oxyhemoglobin (HbO2); precise composition values may depend on a particular organ associated with the vein and metabolic need for oxygen extraction. Arteries can contain primarily oxyhemoglobin (HbO2). A relative absorption of the electromagnetic radiation by a vein ("Uvein") to an absorption by an artery ("Uartery") can be estimated mathematically based on these compositions of venous and arterial blood. This ratio can be used as a measure of venous selectivity of energy absorption for a particular wavelength of radiation.

The absorption ratio of Uvein/Uartery (absorption by veins/absorption by arteries) can be expressed using the absorption by Hb and HbO2 (UHb and UHbO2, respectively). The absorption of the radiation by a vein, Uvein, can be approximated by the following exemplary equation:

$$U\text{vein} = UHbO2 * Sa(v) + UHb * (1 - Sa(v)), \qquad (1)$$

TABLE 1

Absorption of electromagnetic radiation by deoxygenated hemoglobin, Hb, and oxygenated hemoglobin, HbO2.

| Wavelength (nm) | UHb (cm−1/M) | UHbO2 (cm−1/M) | UHb/UHbO2 |
|---|---|---|---|
| 620 | 942 | 6509.6 | 6.910403397 |
| 622 | 858 | 6193.2 | 7.218181818 |
| 624 | 774 | 5906.8 | 7.631524548 |
| 626 | 707.6 | 5620 | 7.942340305 |

TABLE 1-continued

Absorption of electromagnetic radiation by deoxygenated hemoglobin, Hb, and oxygenated hemoglobin, HbO2.

| Wavelength (nm) | UHb (cm−1/M) | UHbO2 (cm−1/M) | UHb/UHbO2 |
|---|---|---|---|
| 628 | 658.8 | 5366.8 | 8.146326655 |
| 630 | 610 | 5148.8 | 8.440655738 |
| 632 | 561.2 | 4930.8 | 8.786172488 |
| 634 | 512.4 | 4730.8 | 9.232630757 |
| 636 | 478.8 | 4602.4 | 9.612364244 |
| 638 | 460.4 | 4473.6 | 9.716768028 |
| 640 | 442 | 4345.2 | 9.830769231 |
| 642 | 423.6 | 4216.8 | 9.954674221 |
| 644 | 405.2 | 4088.4 | 10.08983218 |
| 646 | 390.4 | 3965.08 | 10.15645492 |
| 648 | 379.2 | 3857.6 | 10.17299578 |
| 650 | 368 | 3750.12 | 10.19054348 |
| 652 | 356.8 | 3642.64 | 10.20919283 |
| 654 | 345.6 | 3535.16 | 10.22905093 |
| 656 | 335.2 | 3427.68 | 10.22577566 |
| 658 | 325.6 | 3320.2 | 10.19717445 |
| 660 | 319.6 | 3226.56 | 10.09561952 |
| 662 | 314 | 3140.28 | 10.00089172 |
| 664 | 308.4 | 3053.96 | 9.902594034 |
| 666 | 302.8 | 2967.68 | 9.800792602 |
| 668 | 298 | 2881.4 | 9.669127517 |
| 670 | 294 | 2795.12 | 9.507210884 |
| 672 | 290 | 2708.84 | 9.340827586 |
| 674 | 285.6 | 2627.64 | 9.200420168 |
| 676 | 282 | 2554.4 | 9.058156028 |
| 678 | 279.2 | 2481.16 | 8.886676218 |
| 680 | 277.6 | 2407.92 | 8.674063401 | where Sa(v) can represent the fractional saturation of oxygen in venous blood. In a similar manner, absorption of radiation by n artery, Uartery, can be approximated by the equation:

$$U\text{artery} = UHbO2 \cdot Sa(a) + UHb \cdot (1 - Sa(a)), \quad (2)$$

where Sa(a) can represent the fractional saturation of oxygen in arterial blood.

As described above, Sa(v) can be approximately 0.7 (e.g., a vein may contain approximately 70% oxygenated blood), and Sa(a) can be approximately 1.0 (e.g., blood in an artery can be fully oxygenated). Using these values, the expressions for Uvein and Uartery in Eqs. (1) and (2) can be provided as:

$$U\text{vein} = 0.7\, UHbO2 + 0.3\, UHb, \quad (3)$$

and $$U\text{artery} = UHbO2. \quad (4)$$

The ratio of absorption of radiation by a vein to absorption by an artery, Uvein/Uartery, can then be expressed as:

$$U\text{vein}/U\text{artery} = (0.7\, UHbO2 + 0.3\, UHb)/UHbO2. \quad (5)$$

The absorption ratio Uvein/Uartery can account for the relative composition of deoxyhemoglobin (Hb) and oxyhemoglobin (HbO2) in veins and arteries, and may represent a measure of venous selectivity.

Figure 2:
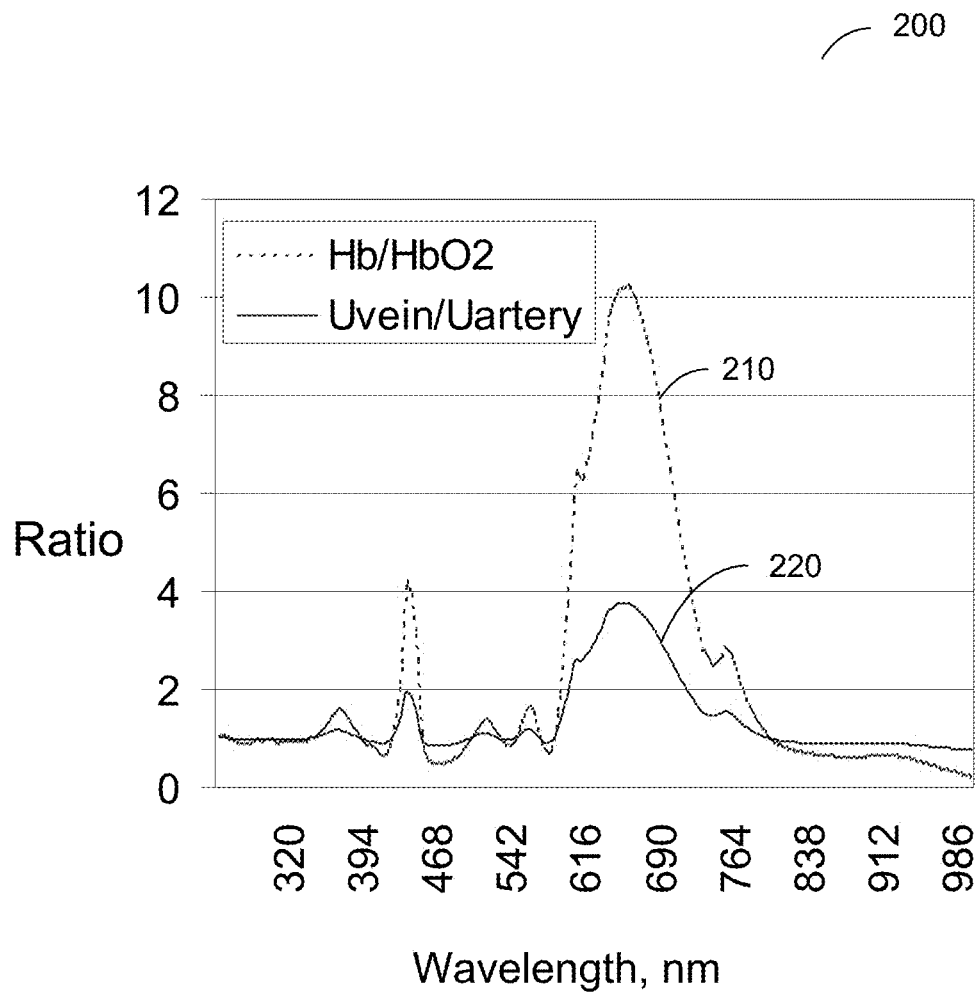
FIG. 2 is an exemplary graph of an absorption ratio of Hb and HbO2, and an absorption ratio of venous and arterial blood, as a function of wavelength of electromagnetic radiation.

FIG. 2 is an exemplary graph 200 showing a ratio 210 of deoxyhemoglobin absorption, UHb, to oxyhemoglobin absorption UHbO2, over a range of wavelengths of electromagnetic radiation. Also shown in FIG. 2 is a selectivity ratio 220, Uvein/Uartery, as a function of radiation wavelength. The absorption selectivity of veins as compared to arteries can reach a maximum value at a wavelength near 650 nm, and may decrease with an increasing or decreasing of the wavelength.

Values of Uvein and Uartery, together with a selectivity ratio Uvein/Uartery, are provided in Table 2 for the radiation wavelengths between 620 nm and 680 nm. This data can indicate that the selectivity ratio Uvein/Uartery may have a maximum value of about 3.77 at a wavelength of about 654 nm. This ratio may remain above 3.7 for wavelengths between about 644 nm and 662 nm, and may be greater than 3.6 for wavelengths between about 638 nm and 668 nm. The selectivity ratio can be greater than 3.3 for wavelengths between about 632 nm and 680 nm.

Based on the absorption data provided herein, the examples of method and system can be provided in accordance with exemplary embodiments of the present invention for non-invasively inducing selective necrosis of unwanted veins, while inducing relatively little or no damage to nearby arteries.

TABLE 2

Absorption of electromagnetic radiation by a vein, Uvein, and an artery, Uartery, together with the selectivity ratio Uvein/Uartery.

| Wavelength (nm) | Uvein (cm−1/M) | Uartery (cm−1/M) | Uvein/Uartery |
|---|---|---|---|
| 620 | 2612 | 942 | 2.77 |
| 622 | 2459 | 858 | 2.87 |
| 624 | 2314 | 774 | 2.99 |
| 626 | 2181 | 708 | 3.08 |
| 628 | 2071 | 659 | 3.14 |
| 630 | 1972 | 610 | 3.23 |
| 632 | 1872 | 561 | 3.34 |
| 634 | 1778 | 512 | 3.47 |
| 636 | 1716 | 479 | 3.58 |
| 638 | 1664 | 460 | 3.62 |
| 640 | 1613 | 442 | 3.65 |
| 642 | 1562 | 424 | 3.69 |
| 644 | 1510 | 405 | 3.73 |
| 646 | 1463 | 390 | 3.75 |
| 648 | 1423 | 379 | 3.75 |
| 650 | 1383 | 368 | 3.76 |
| 652 | 1343 | 357 | 3.76 |
| 654 | 1302 | 346 | 3.77 |
| 656 | 1263 | 335 | 3.77 |
| 658 | 1224 | 326 | 3.76 |
| 660 | 1192 | 320 | 3.73 |
| 662 | 1162 | 314 | 3.70 |
| 664 | 1132 | 308 | 3.67 |
| 666 | 1102 | 303 | 3.64 |
| 668 | 1073 | 298 | 3.60 |
| 670 | 1044 | 294 | 3.55 |
| 672 | 1016 | 290 | 3.50 |
| 674 | 988 | 286 | 3.46 |
| 676 | 964 | 282 | 3.42 |
| 678 | 940 | 279 | 3.37 |
| 680 | 917 | 278 | 3.30 |

For example, a conventional photothermolysis treatment for port wine stains or other vascular lesions can use a pulsed dye laser having a wavelength of about 595 nm. Use of a longer wavelength of about 654 nm, as described herein, can provide increased selectivity of absorption by veins as compared with arteries, and may also allow for a deeper penetration into the treated tissue, which can improve treatment efficacy.

Figure 3:
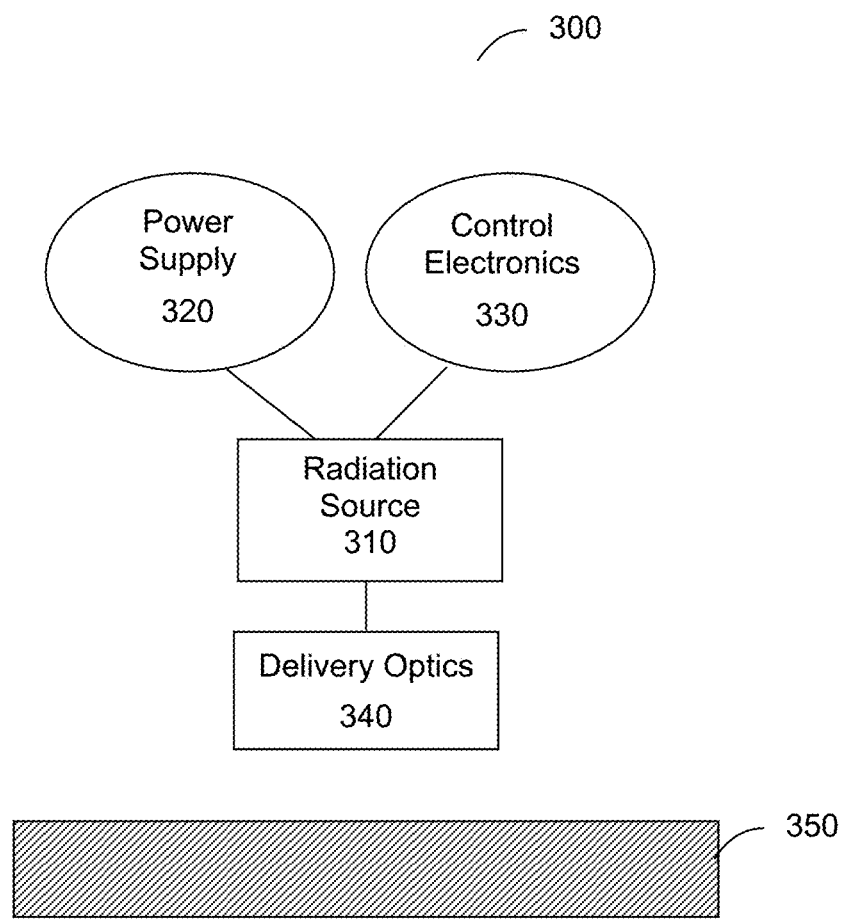
FIG. 3 is a schematic diagram of an exemplary system which may be used in accordance with exemplary embodiments of the present invention.

An example of the system 300 which may be used in accordance with exemplary embodiments of the present invention is shown in FIG. 3. This exemplary system 300 can include a source of electromagnetic radiation 310, a power source 320, a control electronics arrangement 330 and, optionally, a delivery optics arrangement 340. One or more of these components 310-340 may be provided in a single enclosure or a handpiece. Alternatively, one or more of these components 310-340 may be provided in a separate housing from other components.

The power source 320 may be used to provide power to the radiation source 310. The control electronics arrangement 330 can be in electrical or wireless communication with both the power source 320 and the radiation source 310, and can be used to control or affect certain properties of the electromagnetic radiation generated by the radiation source 310. The radiation source 310 can be configured, optionally together with the delivery optics arrangement 340, to direct radiation towards a region of a biological tissue 350 to be treated. The tissue 350 can contain both arteries and veins.

The radiation source 310 can be configured to provide the radiation having a wavelength that is preferentially absorbed by the veins as compared to the arteries. For example, the radiation can have a wavelength between about 632 nm and 680 nm, or preferably between about 638 nm and 668 nm, or more preferably between about 644 nm and 662 nm, or even more preferably about 654 nm.

The radiation source 310 can include a pulsed dye laser configured to provide the radiation having an exemplary wavelength or plurality of wavelengths as described herein. Other types of laser capable of emitting the radiation at one or more preferred wavelengths may also be used. Alternatively, an intense pulsed light (IPL) source can be used. The IPL source may be filtered to provide radiation having wavelengths close to 654 nm, as described herein.

Other radiation source parameters can include pulse duration, fluence, and spot size. These parameters may be selected to be similar to parameters used in conventional photothermolysis techniques, and may be controlled using the control electronics arrangement 330. Fluence of the applied electromagnetic radiation (which can have units of $J/cm^2$) may be selected based on, e.g., the depth and size of a target vein. For example, pulses of the radiation may be used in accordance with exemplary embodiments of the present invention, and can have a duration of, e.g., about 1 to 300 milliseconds, about 10 to 300, or about 20 to 100 milliseconds. Fluence values can be, e.g., between about 20 and 80 $J/cm^2$. These parameters are exemplary, and other values may be used depending on the characteristics of the tissue being treated and the desired degree of thermal damage desired. For example, further exemplary radiation parameters which may be used for photothermolysis of blood vessels are described, e.g., in U.S. Pat, No. 6,306,130.

The delivery optics arrangement 340 can be used to focus the radiation to particular regions within the tissue 350 containing the target vein, in accordance with conventional techniques. Other options may also be used together with the exemplary system 300 including, e.g., an arrangement capable of providing superficial cooling to a surface of the tissue being treated.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced herein are incorporated herein by reference in their entireties.

What is claimed is:

1. A method for treating a region of interest (ROI) of a patient's body, the method comprising:
    identifying an ROI of skin of the patient's body, said identified ROI including at least one venous malformation;
    treating the identified ROI with light having an operational wavelength at which blood in a vein in human skin has an absorption coefficient that is k times higher than an absorption coefficient of a typical artery in human skin such as to photocoagulate said vein by selective photothermolysis of the at least one venous malformation while avoiding damage to an artery within the skin of the ROI,
    a value of k being between 2.77 and 3.50 or greater than or equal 3.6,
    said blood containing about 30 percent of deoxyhemoglobin and about 70 percent oxyhemoglobin.

2. A method according to claim 1, wherein the treating includes treating the identified ROI with light such as to eliminate or reduce perfusion in the at least one venous malformation.

3. A method according to claim 1, wherein the treating includes treating the identified ROI with fluences between about 20 J/cm^2 and about 80 J/cm^2.

4. A method according to claim 1, wherein the treating includes causing thermal damage to the vein of the at least one venous malformation with light generated by a pulsed light source.

5. A method according to claim 1, wherein the treating includes treating the identified ROI with light such as to eliminate or reduce perfusion in the at least one venous malformation.

6. A method according to claim 1, wherein the treating includes treating at least one of a varicose vein and a port wine stain.

7. A method according to claim 1, wherein the treating includes treating the identified ROI with light from at least one of a pulsed dye laser, a wavelength-shifted Nd:YAG laser, a frequency-doubled infrared laser, a high power diode laser array, and a fiber laser.

8. A method according to claim 1, further comprising cooling a surface of said ROI.

9. A method for treating a region of interest (ROI) of a patient's body, the method comprising:
    identifying an ROI of skin of the patient's body, said identified ROI including a venous malformation;
    treating the identified ROI with light having an operational wavelength at which a ratio of absorption of light by deoxygenated hemoglobin of blood in a vein to absorption of light by oxygenated hemoglobin of blood in the vein is between 6.91 and 9.5 or greater than or equal 9.51, so as to photocoagulate the vein by selective photothermolysis of the venous malformation while substantially avoiding damage to an artery in the ROI,
    said blood containing about 30 percent of deoxyhemoglobin and about 70 percent oxyhemoglobin.

10. A method according to claim 9, wherein the treating includes treating the identified ROI with light having an operational wavelength at which said vein in human skin has an absorption coefficient that is at least about 2.7 times higher than an absorption coefficient of a typical artery in human skin.

11. A method according to claim 9, further comprising cooling a surface of said selected ROI.

12. A method according to claim 9, wherein the treating includes treating the venous malformation in said ROI at fluences between about 20 J/cm^2 and about 80 J/cm^2 such as to eliminate or reduce perfusion in the venous malformation.

* * * * *